United States Patent
Jeon et al.

(10) Patent No.: US 11,511,126 B2
(45) Date of Patent: Nov. 29, 2022

(54) APPARATUS FOR MICROWAVE HYPERTHERMIA

(71) Applicant: ELECTRONICS AND TELECOMMUNICATIONS RESEARCH INSTITUTE, Daejeon (KR)

(72) Inventors: Soon Ik Jeon, Sejong (KR); Jang Yeol Kim, Daejeon (KR); Bo Ra Kim, Sejong (KR); Seong-Ho Son, Daejeon (KR); Kwang Jae Lee, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 1085 days.

(21) Appl. No.: 16/158,100

(22) Filed: Oct. 11, 2018

(65) Prior Publication Data

US 2019/0111275 A1    Apr. 18, 2019

(30) Foreign Application Priority Data

Oct. 16, 2017  (KR) .................. 10-2017-0133989
May 16, 2018  (KR) .................. 10-2018-0055920

(51) Int. Cl.
  *A61B 18/12*  (2006.01)
  *A61N 5/02*  (2006.01)
  (Continued)

(52) U.S. Cl.
  CPC ............. *A61N 5/025* (2013.01); *H01Q 1/273* (2013.01); *H05B 6/664* (2013.01); *H05B 6/686* (2013.01);
  (Continued)

(58) Field of Classification Search
  CPC ........... A61N 5/025; A61N 1/40; A61F 5/443; A61F 5/448; H01Q 1/273; H05B 6/664; H05B 6/686
  See application file for complete search history.

(56) References Cited

U.S. PATENT DOCUMENTS 4,471,787 A * 9/1984 Bentall .................. A61N 1/40
                                                 607/154
6,347,251 B1 * 2/2002 Deng ................ A61B 18/1477
                                                 606/41
(Continued)

FOREIGN PATENT DOCUMENTS

JP    2015-119798 A    7/2015

*Primary Examiner* — Joseph J Lauture

(57) ABSTRACT

Provided is a device for microwave hyperthermia that may attach a flexible patch on the skin of a user based on a cross-section of a body tissue of the user, for example, a joint and muscle of a leg and an arm and may emit microwaves towards a plurality of points of the body tissue through the patch. The microwaves emitted toward the body tissue may have the same phase and maximum power. Accordingly, a maximum heat generation point may be generated in an area adjacent to the plurality of points. The device for microwave hyperthermia may move the maximum heat generation point by sequentially changing a phase and a direction of each of the microwaves. The device for microwave hyperthermia may uniformly distribute and maintain heat for treating pain and/or infection over the entire cross-section or a partial area. The device for microwave hyperthermia may be portable.

18 Claims, 8 Drawing Sheets

(51) Int. Cl.
  *H01Q 1/27* (2006.01)
  *H05B 6/66* (2006.01)
  *H05B 6/68* (2006.01)
  H01Q 9/04 (2006.01)
  A61N 1/40 (2006.01)
  A61F 5/448 (2006.01)
  A61F 5/443 (2006.01)

(52) U.S. Cl.
  CPC .............. *A61F 5/443* (2013.01); *A61F 5/448* (2013.01); *A61N 1/40* (2013.01); *A61N 1/403* (2013.01); *H01Q 9/0407* (2013.01)

(56) References Cited

U.S. PATENT DOCUMENTS

| | | |
|---|---|---|
| 6,470,217 B1 | 10/2002 | Fenn et al. |
| 9,079,011 B2 | 7/2015 | Zastrow et al. |
| 2010/0036369 A1* | 2/2010 | Hancock ............ A61B 18/1815 606/33 |
| 2014/0167783 A1 | 6/2014 | Kim et al. |
| 2016/0287086 A1 | 10/2016 | Son et al. |
| 2017/0245929 A1 | 8/2017 | Deem et al. |

* cited by examiner

| | Order | (1) | (2) | (3) | (4) | (5) |
|---|---|---|---|---|---|---|
| 701 | Phase | 0 degrees | 90 degrees | 180 degrees | 270 degrees | 360 degrees |
| Treatment mode A | Patch A | OFF | OFF | OFF | OFF | OFF |
| | Patch B | ON | ON | ON | ON | ON |
| | Patch C | OFF | OFF | OFF | OFF | OFF |
| | Patch D | ON | ON | ON | ON | ON |
| | Timing | t1 | t2 | t3 | t4 | t5 |

| | Order | (1) | | (2) | | (3) | | (4) | | (5) |
|---|---|---|---|---|---|---|---|---|---|---|
| 801 | Phase | 0 degrees | | 90 degrees | | 180 degrees | | 270 degrees | | 360 degrees |
| Treatment mode B | Patch A | OFF | ON | OFF | ON | OFF | ON | OFF | ON | OFF | ON |
| | Patch B | ON | OFF | ON | OFF | ON | OFF | ON | OFF | ON | OFF |
| | Patch C | OFF | ON | OFF | ON | OFF | ON | OFF | ON | OFF | ON |
| | Patch D | ON | OFF | ON | OFF | ON | OFF | ON | OFF | ON | OFF |
| | Timing | t1 | t2 | t3 | t4 | t5 | t6 | t7 | t8 | t9 | t10 |

APPARATUS FOR MICROWAVE HYPERTHERMIA

CROSS-REFERENCE TO RELATED APPLICATION(S)

This application claims the priority benefit of Korean Patent Application No. 10-2017-0133989 filed on Oct. 16, 2017 and Korean Patent Application No. 10-2018-0055920 filed on May 16, 2018 in the Korean Intellectual Property Office, the disclosures of which are incorporated herein by reference for all purposes.

BACKGROUND

1. Field

At least one example embodiment relates to a device for microwave hyperthermia, and more particularly, to a device for microwave hyperthermia that may treat pain and/or infection present over all of or a portion of a cross-section of a body tissue of a user by attaching a plurality of flexible microwave patches on the skin of the user based on the cross-section of the body tissue in a plurality of directions.

2. Description of Related Art

A thermotherapy device according to the related art may include elements configured to treat cancer and lesions, etc., and may induce microwaves toward lesions of a body tissue of a user. The thermotherapy device may monitor and control whether microwaves are normally induced toward lesions and used to generate heat.

Also, the thermotherapy device may be inconvenient for the user to easily carry and use, and may cause pain of the user, for example, a patient. That is, the thermotherapy device needs to control a microwave at a relatively high output intensity to treat cancer and lesions, etc., present at a single point of the body tissue, and monitors a temperature in the body tissue based on the intensity of microwave. The thermotherapy device needs to cool heat generated on the skin using a blowing air conditioning device to relieve the pain of the user. Since emitting of microwaves, monitoring of temperature, and cooling need to be performed at the same time, the thermotherapy device may be in a complex structure for the user to directly use.

Further, the thermotherapy device includes a patch to emit microwaves towards an inside of the body tissue of the user. The patch is attached on the skin of the user. With the patch being attached on the skin, microwaves emitted from the thermotherapy device may be transferred to the inside of the body tissue using the air as a medium. Here, mismatching of microwaves may occur between the patch and the skin on which the patch is attached. Damage, for example, burn may occur on the skin due to heat caused by the mismatching. Accordingly, the thermotherapy device cools the heat using the blowing air to decrease the heat generated on the skin. However, if the heat is cooled, the treatment effect of the thermotherapy device may be degraded.

The thermotherapy device emits radio waves toward a specific point of the body tissue using two waveguide antennas, respectively, in order to perform thermal treatment on a plurality of points of the body tissue. Here, each radio wave emitted toward the specific point of the body tissue has a fixed phase in a different direction. In this case, the thermotherapy device may not generate heat that is uniformly distributed over the wide-range area from the body tissue of, for example, a joint, muscle, etc., of a leg, an arm, etc.

Also, the thermotherapy device needs to bi-directionally compress a target to be treated using a compression plate used to smoothly perform radio wave transmission of a waveguide antenna, which may cause inconveniences for a user, for example, a patient. Accordingly, there is a need for a device for microwave hyperthermia that may treat pain, inflammation, and the like.

SUMMARY

At least one example embodiment provides a device for microwave hyperthermia that may reduce or treat pain or inflammation occurring over a wide range area of a deep portion of a body tissue, for example, a joint, muscle, etc., of a leg, an arm, etc., of a user using warm heat that is uniformly distributed and maintained.

At least one example embodiment also provides a device for microwave hyperthermia that is provided in a simple function and configuration for a user to easily and readily use.

According to an aspect of an example embodiment, there is provided a device for microwave hyperthermia, the device including a power device configured to supply power; a user input device configured to receive an input on a treatment mode of the device for microwave hyperthermia for treating an affected area present in a body tissue of a user; and a microwave control device configured to control a microwave for generating a heat in a deep portion of the body tissue through n patches attached on the skin of the user. The microwave control device is configured to control the microwave to shift a phase of the microwave emitted in each of directions in which the n patches are attached on the skin of the user shifts based on the treatment mode.

The microwave control device may include a microwave generator configured to generate the microwave; a phase shifter configured to shift the phase of the microwave based on the treatment mode; a switcher configured to switch at least one of the n patches to emit the phase-shifted microwave; and a microwave outputter configured to output the phase-shifted microwave through a cable that is connected to each of the switched at least one patch.

The phase shifter may be configured to shift the phase of the microwave emitted in each of the directions to have a desired phase difference at each timing at which the microwave is output within an operation time of the treatment mode.

The phase shifter may be configured to shift the phase of the microwave based on the phase of the microwave that is to be output through each of the n patches based on each corresponding timing.

The phase of the microwave may change a generation location and a distribution range of heat from the skin of the user to the deep portion of the body tissue.

The switcher may be configured to switch a direction in which the microwave is emitted so that the phase-shifted microwave is output through at least one of the n patches based on each corresponding timing.

The microwave outputter may be configured to amplify the phase-shifted microwave and to output the amplified microwave through the cable that is connected to each of the switched at least one patch.

Each of the n patches may be configured to receive the microwave of which the phase is shifted based on the treatment mode, and to emit the received microwave from the skin of the user toward the inside of the body tissue.

The microwave may be emitted through at least one of the n patches and may have the same phase at a plurality of points occurring in the deep portion of the body tissue.

According to another aspect of at least one example embodiment, there is provided a patch configured to connect to a device for microwave hyperthermia, the patch including a surface cover configured to control a microwave transferred through a cable that is connected to the device for microwave hyperthermia; a patch antenna including a dielectric configured to transfer the microwave to a deep portion of a body tissue of a user; and a contactor configured to contact the surface cover and to transfer the microwave reflected from the surface cover to the patch antenna. The patch is configured to emit a microwave having a desired phase difference toward the deep portion of the body tissue based on each timing at which the microwave is output based on a treatment mode of the device for microwave hyperthermia.

The surface cover may be configured to block leakage of the microwave to be emitted toward the deep portion of the body tissue of the user or to reflect the microwave toward the deep portion of the body tissue.

The dielectric may perform radio frequency (RF) matching between the patch antenna and the skin of the user and may include a medium for providing thermoelectric cooling or water cooling by heat exchange on the skin of the user.

An adhesive material may be applied on one surface of the patch antenna to be attached on the skin of the user.

According to another aspect of at least one example embodiment, there is provided a microwave control device included in a device for microwave hyperthermia, the microwave control device including a microwave generator configured to generate a microwave based on a treatment mode of the device for microwave hyperthermia for treating an affected area present in a body tissue of a user; a phase shifter configured to shift a phase of the microwave emitted in each of directions in which n patches are attached on the skin of the user based on the treatment mode; a switcher configured to switch at least one of the n patches to emit the phase-shifted microwave; a microwave amplifier configured to amplify the phase-shifted microwave; and a microwave outputter configured to output the amplified microwave through a cable that is connected to each of the switched at least one patch. The phase shifter is configured to shift the phase of the microwave emitted in each of the directions to have a desired phase difference at each timing at which the microwave is output within an operation time of the treatment mode.

The phase shifter may be configured to shift the phase of the microwave based on the phase of the microwave that is to be output through each of the n patches based on each corresponding timing.

The phase of the microwave may change a generation location and a distribution range of heat from the skin of the user to the deep portion of the body tissue.

The switcher may be configured to switch a direction in which the microwave is emitted so that the phase-shifted microwave is output through at least one of the n patches based on each corresponding timing.

Each of the n patches may be configured to receive the microwave of which the phase is shifted based on the treatment mode, and to emit the received microwave from the skin of the user toward the inside of the body tissue.

The microwave may be emitted through at least one of the n patches and may have the same phase at a plurality of points occurring in the deep portion of the body tissue.

According to example embodiments, it is possible to reduce or treat pain or inflammation occurring over a wide range area by emitting a microwave so that warm heat may be uniformly distributed and maintained from a deep portion of a cross-section of a joint, muscle, etc., of a leg, an arm, etc., of a user to the skin of the user.

BRIEF DESCRIPTION OF THE DRAWINGS

These and/or other aspects, features, and advantages of the invention will become apparent and more readily appreciated from the following description of example embodiments, taken in conjunction with the accompanying drawings of which.

DETAILED DESCRIPTION

Figure 1:
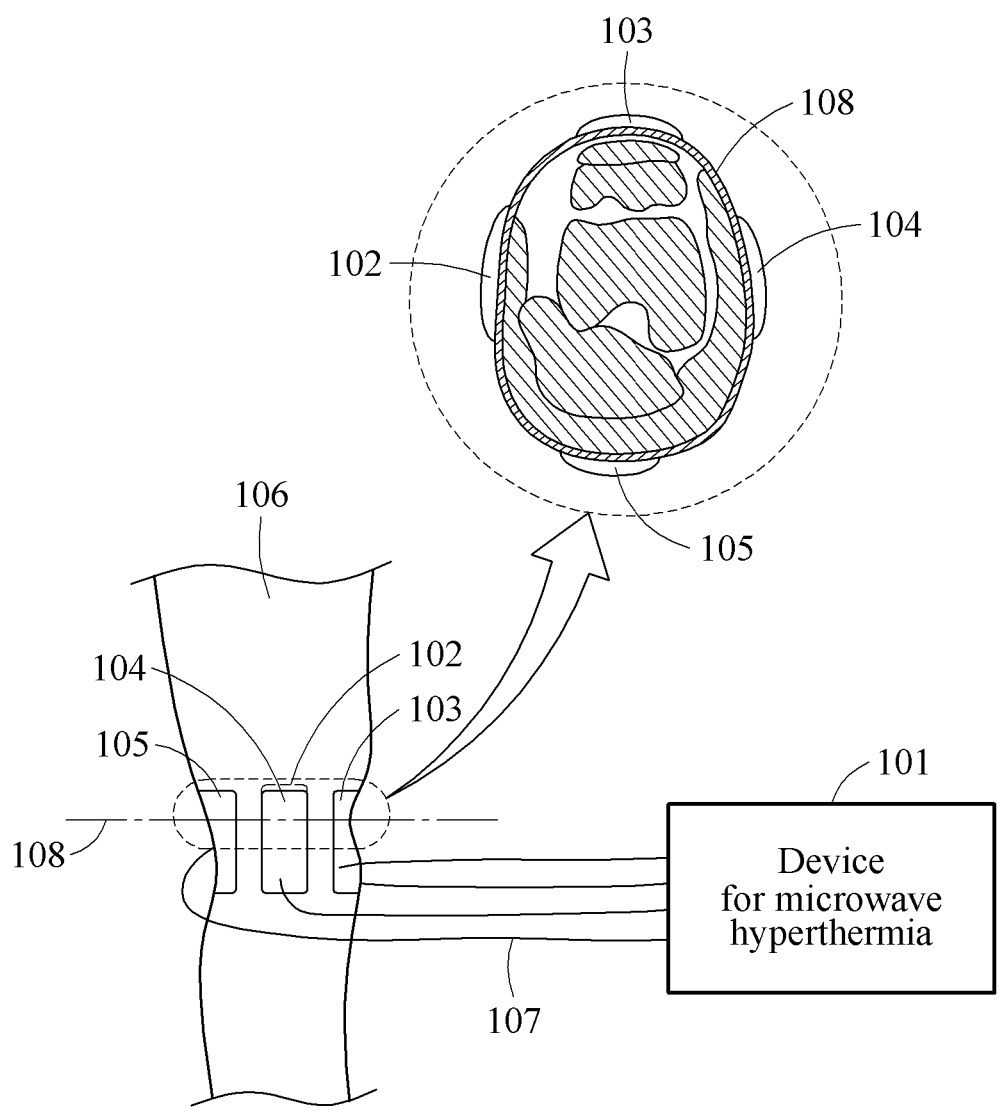
FIG. 1 illustrates an example of a device for microwave hyperthermia for treating an affected area present in a body tissue of a user according to an example embodiment.

Hereinafter, some example embodiments will be described in detail with reference to the accompanying drawings. The following detailed structural or functional description of example embodiments is provided as an example only and various alterations and modifications may be made to the example embodiments. Accordingly, the example embodiments are not construed as being limited to the disclosure and should be understood to include all changes, equivalents, and replacements within the technical scope of the disclosure.

Terms, such as first, second, and the like, may be used herein to describe components. Each of these terminologies is not used to define an essence, order or sequence of a corresponding component but used merely to distinguish the corresponding component from other component(s). The singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

Unless otherwise defined, all terms, including technical and scientific terms, used herein have the same meaning as commonly understood by one of ordinary skill in the art to which this disclosure pertains. Terms, such as those defined in commonly used dictionaries, are to be interpreted as having a meaning that is consistent with their meaning in the context of the relevant art, and are not to be interpreted in an idealized or overly formal sense unless expressly so defined herein.

Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

FIG. 1 illustrates an example of a device for microwave hyperthermia for treating an affected area present in a body tissue of a user according to an example embodiment.

Referring to FIG. 1, a device for microwave hyperthermia 101 may be connected to patches 102, 103, 104, and 105 attached on the skin of a user 106. The device for microwave hyperthermia 101 may emit microwaves toward an affected area present in a body tissue of the user 106 through the patches 102, 103, 104, and 105.

In detail, each of the patches 102, 103, 104, and 105 may be a medium attached on the skin of the user 106 to be treated to transfer current. Here, the body tissue of the user 106 may include a disease or a wounded area in a leg, an arm, a joint, muscle, etc., of the user 106.

The patches 102, 103, 104, and 105 may be attached on the skin of the user 106 based on a cross-section 108 of the body tissue of the user 106 to treat the affected area present in the body tissue of the user 106.

In general, the inside of the body tissue may include sinew, bone, fat, skin, muscle, and the like, based on the cross-section 108 of the body tissue. The user 106 may suffer from pain or inflammation occurring due to a disease or a wound among the above areas, for example, the sinew, the bone, the fat, the skin, muscle, and the like.

Accordingly, the user 106 may use the patches 102, 103, 104, and 105 as media capable of transferring microwaves for treatment. The patches 102, 103, 104, and 105 may be attached on the skin on which the pain or the inflammation occurs. Here, the microwaves may be reflected from the patches 102, 103, 104, and 105 and emitted toward the affected area or an area adjacent to the affected area to relieve or ease the pain or the inflammation from which the user 106 suffers. Here, n patches including the patches 102, 103, 104, and 105 may be present. Each of the n patches may be connected to a microwave connection cable 107 and may receive a microwave from the device for microwave hyperthermia 101.

Each of the patches 102, 103, 104, and 105 may emit the microwave transferred through the device for microwave hyperthermia 101 toward a deep portion of the body tissue of the user 106 and may induce warm heat to be generated in the affected area in which the pain or the inflammation occurs or the area adjacent to the affected area. The warm heat generated by microwaves emitted from the patches 102, 103, 104, and 105 may be distributed over the affected area or the area adjacent thereto. According to example embodiments, it is possible to relieve or treat pain or inflammation of the user 106 by maintaining the generated warm heat in the affected area in which the pain or the inflammation occurs or the area adjacent thereto based on a treatment mode for emitting microwaves.

Herein, using the device for microwave hyperthermia 1, the user 106 may easily and conveniently relieve or treat pain or inflammation occurring over a relatively wide area of, for example, a joint, muscle, etc., of a leg, an arm, etc., of the user 1.

The device for microwave hyperthermia 101 may emit microwaves in a plurality of directions based on the cross-section 108, for example, a joint and muscle of a leg and an arm. Microwaves emitted toward a deep portion of the body tissue of the user 106 may have the same phase at a plurality of points in the deep portion and power may be maximized at the same phase. Also, a maximum heat generation point may be generated in an area adjacent to the plurality of points toward which the microwaves are emitted.

The device for microwave hyperthermia 101 may use a treatment mode. In the treatment mode, microwaves may be emitted toward the deep portion of the body tissue based on a treatment purpose of the user 106 and a phase and an emission direction of the microwave may be in a programmed state.

The device for microwave hyperthermia 101 may emit microwaves toward the deep portion of the body tissue based on the phase and the direction of the microwave that is programmed according to the treatment mode. Here, a phase and an emission direction of each microwave may sequentially vary in pre-programmed order. The maximum heat generation point may sequentially move within the cross-section 108 of the body tissue based on the direction and the phase of each microwave emitted toward the deep portion of the body tissue. Through this, the device for microwave hyperthermia 101 may uniformly distribute or maintain the warm heat for treating the pain or the inflammation over the entire or a portion of the cross-section 108 of the body tissue of the user 106.

Also, the device for microwave hyperthermia 101 may emit various types of microwaves based on the phase and the direction of microwaves programmed according to the treatment mode. Also, the device for microwave hyperthermia 101 may have a simple configuration, for example, may include at least one phase controller, a signal switcher, and a signal distributor. The configuration is further described with reference to FIGS. 5 and 6.

Also, the device for microwave hyperthermia 101 may use a patch-typed medium to be attached on the skin of the user 106 as a medium of emitting a microwave, and may also include dielectric liquid having a dielectric permittivity similar to that of the body tissue to be treated. Here, the device for microwave hyperthermia 101 may apply a relatively low output to the warm heat generated in the deep portion to be readily used by the user 106. Also, the device for microwave hyperthermia 101 may attach the plurality of patches 102, 103, 104, and 105 on the skin to treat an affected area of the body tissue, for example, a joint and muscle of a leg and an arm, and may employ a water cooling method of using dielectric liquid contained in the patches 102, 103, 104, and 105 attached on the skin as cooling media.

In the patch 102, 103, 104, 105 to be attached on the skin, a flexible microwave patch antenna may constitute a layer. Each of the patches 102, 103, 104, and 105 attached on the skin may include a medium that contains dielectric liquid having a dielectric permittivity similar to that of the body tissue to be treated. Also, an adhesive material may be applied over the patches 102, 103, 104, and 105 so that the medium may be attached on the body tissue of, for example, a joint and muscle of a leg and an arm. Accordingly, similar to a pain relief patch, the patches 102, 103, 104, and 105 may be easily and conveniently used.

Figure 2:
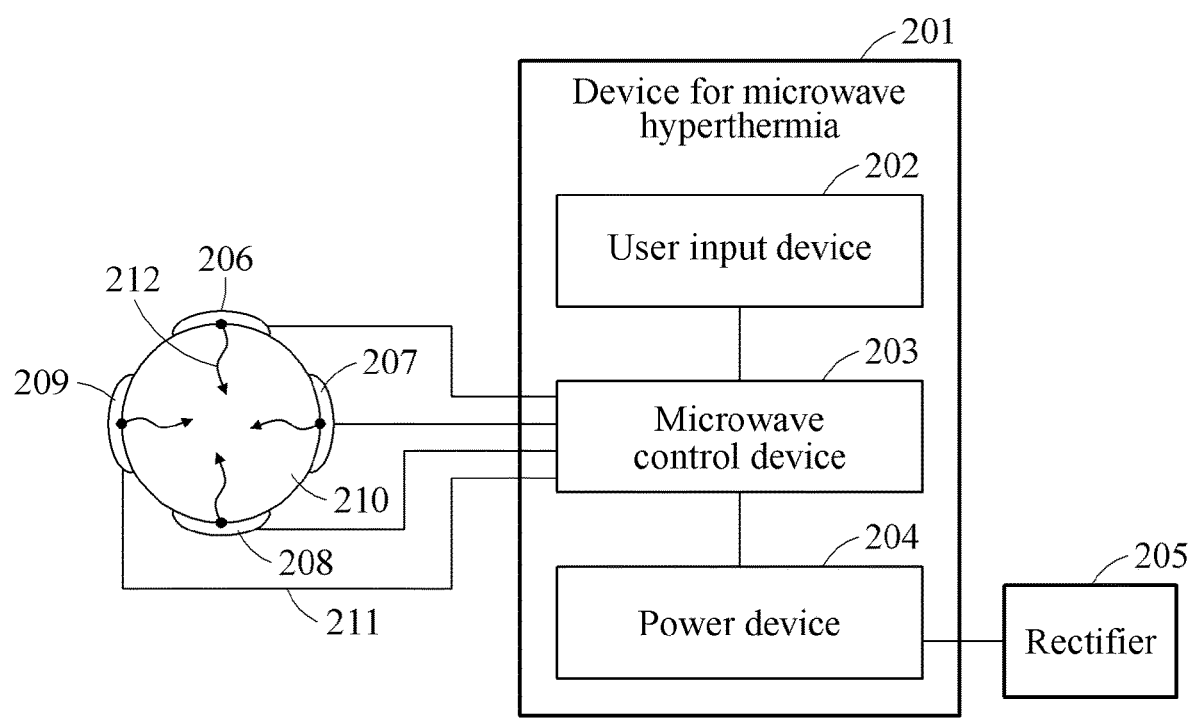
FIG. 2 is a diagram illustrating an example of a configuration of a device for microwave hyperthermia according to an example embodiment.

FIG. 2 is a diagram illustrating an example of a configuration of a device for microwave hyperthermia according to an example embodiment.

Referring to FIG. 2, n patches including patches 206, 207, 208, and 209 may be attached on the skin of a user based on a cross-section of a body tissue of the user. The user may attach the n patches including the patches 206, 207, 208, and 209 to be separate at desired intervals based on an affected area in which pain and/or inflammation occurs. Here, an adhesive material may be applied over one surface of each of the n patches to be readily attached on the skin of the user and may be detachably attached and movable on the skin of the user if necessary. Once the n patches including the patches 206, 207, 208, and 209 are attached on the skin of the user, each of the n patches may be fixed at a corresponding location until an external force is applied and may emit microwaves transferred from a device for microwave hyperthermia 201 toward a deep portion of a body tissue of the user.

In detail, each of the n patches including the patches 206, 207, 208, and 209 may be a medium of transferring current, a microwave may be output from the device for microwave hyperthermia 201 and may pass through at least one of the n patches. Here, an emission direction 212 of a microwave may vary. For example, the emission direction 212 of the microwave may be changed toward an inside of the body tissue and the microwave may be emitted toward the deep portion of the body tissue through a corresponding patch.

To this end, each of the n patches including the patches 206, 207, 208, and 209 may be connected to one surface of a microwave connection cable 211 capable of transferring a microwave and another surface of the microwave connection cable 211 may be connected to the device for microwave hyperthermia 201.

The device for microwave hyperthermia 201 may sequentially shift a phase of a microwave transferred to each of the n patches including the patches 206, 207, 208, and 209, may switch the phase-shifted microwave and may output the same to each of the n patches including the patches 206, 207, 208, and 209.

To this end, the device for microwave hyperthermia 201 may include a user input device 202, a microwave control device 203, and a power device 204.

The user input device 202 may provide a user desiring to be treated with state information of the device for microwave hyperthermia 201, power information of the device for microwave hyperthermia 201, and selection information for determining a treatment mode of the device for microwave hyperthermia 201. Here, the user input device 202 may display the state information, the power information, and the selection information on a display.

The state information may refer to information indicating a situation in which the device for microwave hyperthermia 201 currently operates. For example, the state information may correspond to operation information of the microwave control device 203 as information used to determine a current operation of the device for microwave hyperthermia 201, such as a standby state, a ready state, a warm heating state, and a warm heat maintaining state, and the like.

The power information may refer to information associated with power ON/OFF in conjunction with the power device 204. For example, the power information may be information used to indicate a current ON/OFF state of the device for microwave hyperthermia 201.

The selection information may refer to information indicating a selected treatment mode if the user selects a treatment mode of the device for microwave hyperthermia 201 for treating an affected area present in the body tissue of the user. For example, the treatment mode of the device for microwave hyperthermia 201 may include a variety of schemes based on a phase of a microwave to be emitted, a use pattern of a patch toward which the microwave is emitted, and the like.

The microwave control device 203 may sequentially shift a phase of a microwave transferred to each of the n patches including the patches 206, 207, 208, and 209. Here, the microwave control device 203 may shift the phase of the microwave based on the treatment mode input as the selection information from the user input device 202. The microwave control device 203 may output the phase-shifted microwave by selecting a direction in which the phase-shifted microwave is emitted based on a predetermined path for transferring the phase-shifted microwave and by performing switching.

The power device 204 may supply power to the user input device 202 and the microwave control device 203. For example, the power device 204 may be a battery configured to charge the power from an outside or to supply current autonomously. The power device 204 may be connected to a rectifier 205 provided at an outside and configured to convert alternating current (AC) to direct current (D) and to supply the power to the power device 204.

Figure 3:
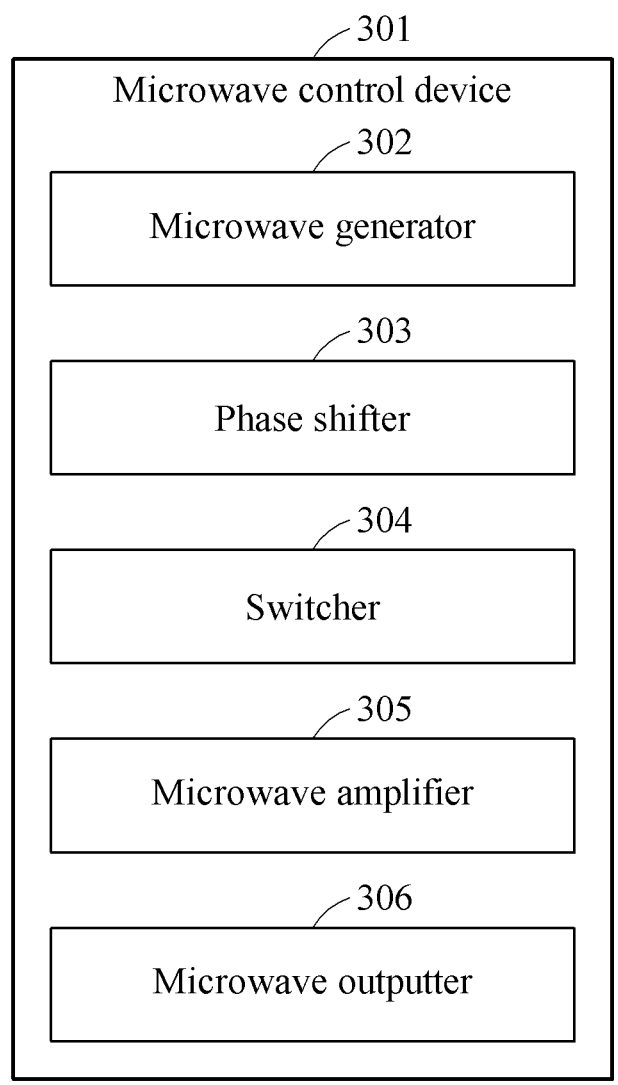
FIG. 3 is a diagram illustrating an example of a configuration of a microwave control device included in a device for microwave hyperthermia according to an example embodiment.

FIG. 3 is a diagram illustrating an example of a configuration of a microwave control device included in a device for microwave hyperthermia according to an example embodiment.

Referring to FIG. 3, a microwave control device 301 may include a microwave generator 302, a phase shifter 303, a switcher 304, a microwave amplifier 305, and a microwave outputter 306.

The microwave generator 302 may generate a microwave to treat an affected area present in a deep portion of a body tissue of a user based on a treatment mode input through a user input device. Here, the microwave may be a basic signal emitted through each of n patches attached on the skin of the user. For example, the microwave generator 302 may generate a microwave with a phase of zero degrees.

The phase shifter 303 may shift the phase of the microwave generated by the microwave generator 302. In detail, the phase shifter 303 may shift the phase of the microwave based on the treatment mode of the device for microwave hyperthermia input from the user input device and for treating the affected area present in the body tissue of the user.

The treatment mode may refer to a specific state that is programmed to treat the affected area present in the body tissue of the user. For example, a treatment mode A may refer to a method that is programmed to generate heat in one direction relative to the affected area present in the body tissue of the user. As another example, a treatment mode B may refer to a method that is programmed to generate heat in a cross form relative to the affected area present in the body tissue of the user.

The phase shifter 303 may shift the phase of the microwave to form a heat distribution area and a heat maintenance area of heat generated in the deep portion of the body tissue of the user by the device for microwave hyperthermia based on the treatment mode. That is, the phase shifter 303 may shift the phase of the microwave emitted in each of the directions to have a desired phase difference at each timing at which the microwave is output within an operation time of the treatment mode. Also, the phase shifter 303 may shift the phase of the microwave based on the phase of the microwave that is to be output through each of the n patches based on each corresponding timing.

Here, the phase of the microwave may be a condition capable of changing a heat generation location and a heat distribution range from the skin of the user to the deep portion of the body tissue of the user.

The switcher 304 may switch at least one of the n patches to emit the phase-shifted microwave. That is, the switcher 304 may switch a direction in which the microwave is emitted so that the phase-shifted microwave may be output through at least one of the n patches based on each corresponding timing.

The microwave amplifier 305 may amplify the phase-shifted microwave. The microwave amplifier 305 may amplify the phase-shifted microwave so that the microwave may be emitted toward the deep portion of the body tissue.

The microwave outputter 306 may output the phase-shifted microwave through a cable that is connected to each of the switched at least one patch. The microwave outputter 306 may output the amplified microwave through the cable that is connected to each of the switched at least one patch.

The output microwave may be transferred to a single patch connected to the cable through the cable and the patch to which the microwave is transferred may reflect the microwave to be emitted toward the deep portion of the body tissue of the user. The microwave may be emitted through at least one of the n patches and may have the same phase at a plurality of points occurring in the deep portion of the body tissue.

Figure 4:
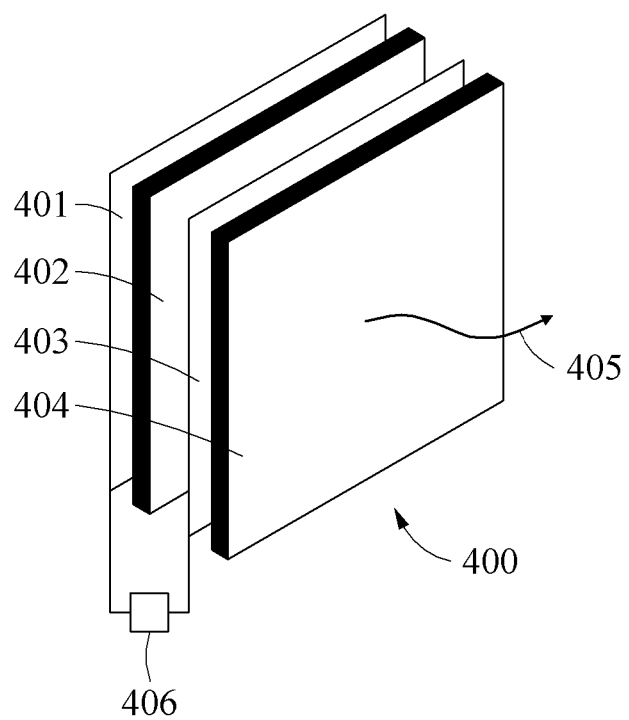
FIG. 4 illustrates an example of a patch connected to a device for microwave hyperthermia according to an example embodiment.

FIG. 4 illustrates an example of a patch connected to a device for microwave hyperthermia according to an example embodiment.

Referring to FIG. 4, a patch 400 may be attached on the skin of a user as a component of a device for microwave hyperthermia. The patch 400 may include a surface cover 401, a patch antenna, and a contactor 406.

The surface cover 401 may control a microwave transferred through a cable that is connected to the device for microwave hyperthermia. That is, the surface cover 401 may block leakage of a microwave to be emitted toward a deep portion of a body tissue of the user, or may reflect the microwave toward the deep portion of the body tissue of the user. For example, the surface cover 401 may include a flexible aluminum foil layer as a conductive layer.

The patch antenna may be an antenna including a dielectric capable of transferring the microwave toward the deep portion of the body tissue of the user. In detail, the dielectric may perform radio frequency (RF) matching between the patch antenna and the skin of the user and may provide thermoelectric cooling or water cooling by heat exchange on the skin of the user. For example, the patch antenna may include a flexible dielectric layer 402 having the dielectric permittivity of 50 and the conductivity of 0.5 as a gelatin component containing moisture and a patch layer 403 on which a conductive material is printed.

Here, the patch 400 may have a dielectric permittivity similar to that of the body tissue to be treated and may perform RF matching between the patch antenna and the skin surface. The patch 400 may be used as a medium that contains liquid and provides a thermoelectric cooling or water cooling effect. An adhesive material may be applied over the patch 400 to be attached on the skin, for example, a joint, muscle, etc., of a leg, an arm, etc. That is, the patch 400 may include a flexible adhesive layer 404 having the dielectric permittivity of 50 and the conductivity of 0.5 as a gelatin component.

The contactor 406 may contact the surface cover 401 and may transfer a microwave to the patch antenna through connection to a microwave connection cable.

The patch 400 may be configured as above and may be attached on the skin of the user, such as a general pain relief patch. Further, the patch 400 may be easily attachable and detachable due to the adhesive layer 404. A microwave for treating pain and inflammation occurring in a joint or muscle of a leg or an arm may be emitted from the attached patch 400 toward a direction 405 corresponding to the deep portion of the body tissue of the user.

Figure 5:
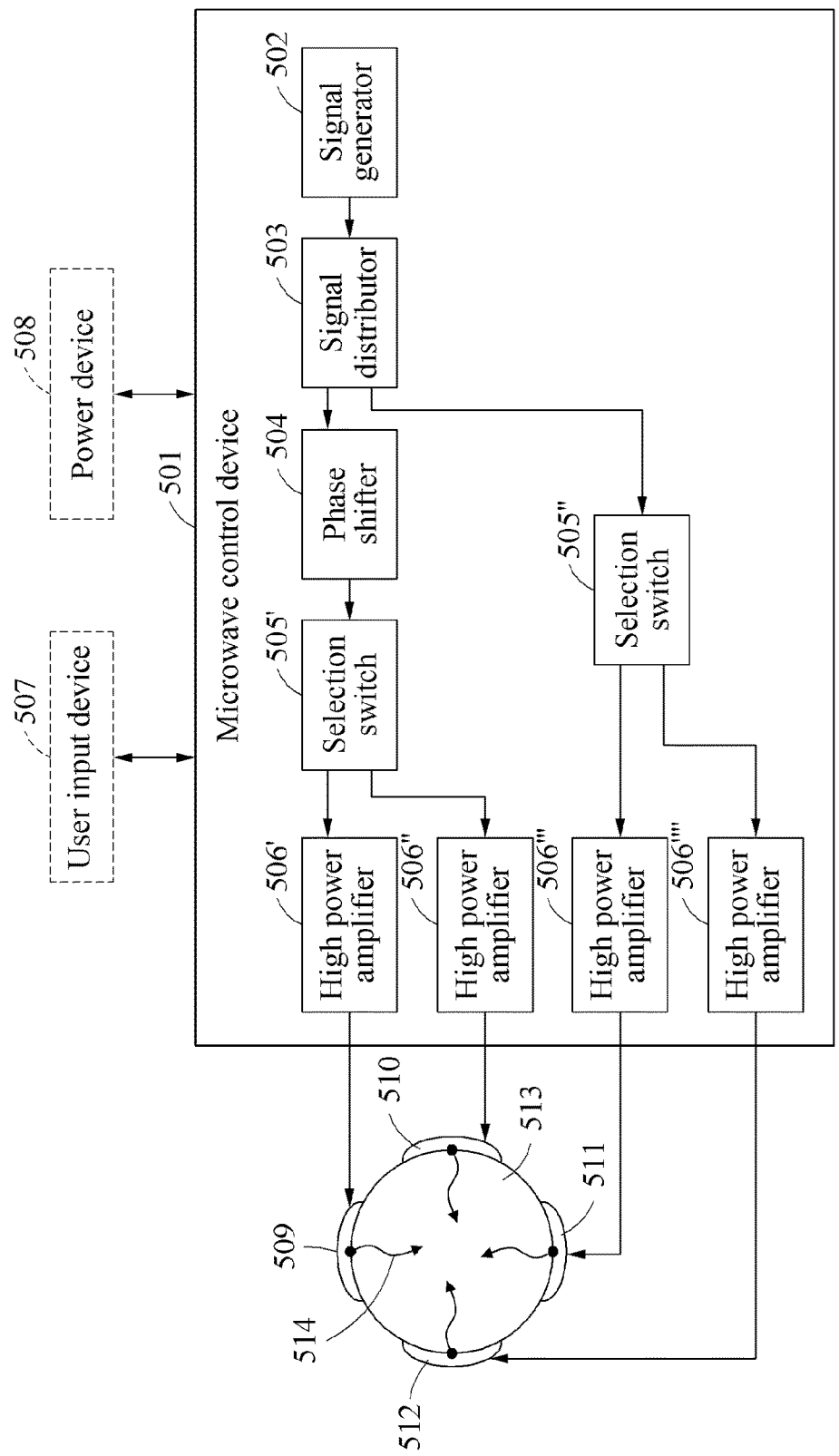
FIG. 5 is a diagram illustrating an example of a configuration of a microwave control device according to an example embodiment.

FIG. 5 is a diagram illustrating an example of a configuration of a microwave control device according to an example embodiment.

Referring to FIG. 5, a device for microwave hyperthermia may include a user input device 507, a power device 508, and a microwave control device 501.

The user input device 507 may receive an input on a treatment mode for a desired portion 513 to be treated from a user.

The power device 508 may supply power or block the supply of the power to the microwave control device 501 based on a control signal input from the user input device 507. For example, the power device 508 may supply the power to the microwave control device 501 in response to the treatment mode input from the user input device 507.

The microwave control device 501 may include a signal generator 502, a signal distributor 503, a phase shifter 504, selection switches 505' and 505", and high power amplifiers 506', 506", 506''', and 506''''.

The signal generator 502 may correspond to the microwave generator 302 of FIG. 3. Here, the signal generator 502 may generate a microwave signal used to generate radio heat in a deep portion of a body tissue of the user based on the treatment mode input from the user input device 507.

The signal distributor 503 may correspond to the phase shifter 303 of FIG. 3. The signal distributor 503 may divide a propagation path of the microwave received from the signal generator 502. That is, the signal distributor 503 may divide the propagation path of the microwave into a path for fixing the microwave and a path for shifting a phase of the microwave at the phase shifter 504.

Here, the signal distributor 503 may verify each timing at which the microwave is output within an operation time of the treatment mode, and may identify a patch for outputting the phase-shifted microwave and a patch for outputting the generated microwave at each timing. That is, the signal distributor 503 may verify each point in time at which the phase of the microwave needs to be shifted based on a programmed treatment mode. At each point in time, the signal distributor 503 may generate Q groups, each group M (M=1, 2, 3, . . . P, P<N) patches. Here, Q denotes an integer.

The signal distributor 503 may classify each of the generated Q groups into a corresponding propagation path based on each timing and may transfer a microwave to each group. Here, the transferred microwave may have a phase of zero degrees.

The phase shifter 504 may correspond to the phase shifter 303 of FIG. 3. The phase shifter 504 may shift the phase of the microwave input from the signal distributor 503. Here, the phase shifter 504 may shift the phase of the microwave based on a control signal preprogrammed according to the treatment mode. That is, the phase shifter 504 may sequentially shift the phase of the microwave in preset order according to each timing at which the microwave is output within an operation time of the treatment mode.

The selection switches 505' and 505" may correspond to the switcher 304 of FIG. 3. Each of the selection switches 505' and 505" may switch a signal path to output the microwave. For example, each of the selection switches 505' and 505" may switch ON or OFF a path of the microwave based on a patch for outputting the microwave at each timing of the treatment mode. For example, each of the selection switches 505' and 505" may switch ON or OFF the path of the microwave based on a control signal programmed according to the treatment mode.

Here, the selection switch 505' may switch a signal path to the high power amplifier 506', 506" under the programmed control as an optimal path for outputting the phase-shifted microwave.

Also, the selection switch 505" may switch the signal path to the high power amplifier 506''', 506'''' under programed control as an optimal path for outputting the microwave transferred from the signal distributor 503 and of which the phase is not shifted.

The high power amplifiers 506', 506", 506''', and 506'''' may correspond to the microwave amplifier 305 and the microwave outputter 306 of FIG. 3. The high power amplifiers 506', 506", 506''', and 506'''' may be connected to a patch A 509, a patch B 510, a patch C 511, and a patch D 512, respectively. The user may attach the patch A 509, the patch B 510, the patch C 511, and the patch D 512 on the skin of the user based on a cross-section of the body tissue of the user.

Each of the high power amplifiers 506', 506", 506''', and 506'''' may amplify the microwave that is switched and transferred from the selection switch 505', 505". The high power amplifiers 506', 506", 506''', and 506'''' may output the amplified microwaves to the patch A 509, the patch B 510, the patch C 511, and the patch D 512, respectively.

For example, the high power amplifier 506' may be connected to the patch A 509, the high power amplifier 506" may be connected to the patch B 510, the high power amplifier 506''' may be connected to the patch C 511, and the high power amplifier 506'''' may be connected to the patch D 512. Each of the high power amplifiers 506', 506", 506''', and 506'''' may amplify the power of the microwave based on whether switching is performed and may output the amplified microwave to each corresponding patch. The microwave may be transferred from each of the patch A 509, the patch B 510, the patch C 511, and the patch D 512 toward a direction 514 corresponding to the deep portion of the body tissue of the user.

Figure 6:
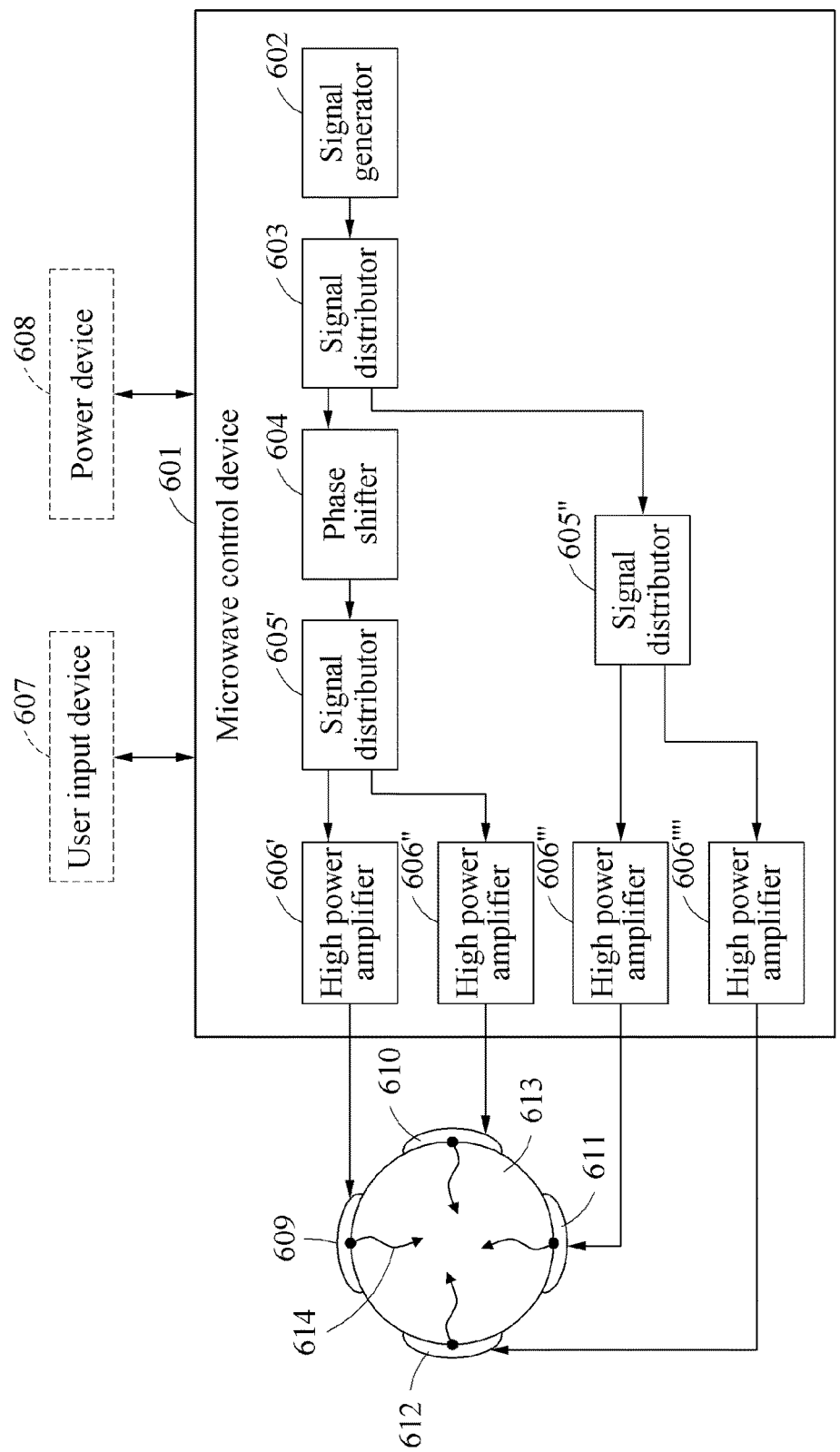
FIG. 6 is a diagram illustrating another example of a configuration of a microwave control device according to an example embodiment.

FIG. 6 is a diagram illustrating another example of a configuration of a microwave control device according to an example embodiment.

Referring to FIG. 6, a device for microwave hyperthermia may include a user input device 607, a power device 608, and a microwave control device 601.

The user input device 607 may receive an input on a treatment mode for a desired portion 613 to be treated from a user.

The power device 608 may supply power or block supply of the power to the microwave control device 601 based on a control signal input from the user input device 607. For example, the power device 608 may supply the power to the microwave control device 601 in response to the treatment mode input from the user input device 607.

The microwave control device 601 may include a signal generator 602, a signal distributor 603, a phase shifter 604, signal distributors 605' and 605", and high power amplifiers 606', 606", 606''', and 606''''.

The signal generator 602 may correspond to the microwave generator 302 of FIG. 3. The signal generator 602 may generate a microwave signal used to generate radio heat in a deep portion of a body tissue of the user based on the treatment mode input from the user input device 607.

The signal distributor 603 may correspond to the phase shifter 303 of FIG. 3. The signal distributor 603 may divide a propagation path of the microwave received from the signal generator 602. That is, the signal distributor 603 may divide the propagation path of the microwave into a path for fixing the microwave and a path for shifting a phase of the microwave at the phase shifter 604.

The phase shifter 604 may correspond to the phase shifter 303 of FIG. 3. The phase shifter 604 may shift the phase of the microwave input from the signal distributor 603. Here, the phase shifter 604 may shift the phase of the microwave based on a control signal preprogrammed according to the treatment mode.

Each of the signal distributors 605' and 605" may distribute a signal path to output the microwave. For example, each of the signal distributors 605' and 605" may distribute a path of the microwave passing through the corresponding signal distributor 605', 605" based on a patch for outputting the microwave at each timing of the treatment mode.

Here, the signal distributor 605' may distribute a signal path to the high power amplifier 606', 606" under programmed control as a final path for outputting the phase-shifted microwave.

Also, the signal distributor 606" may distribute the signal path to the high power amplifiers 606''' and 606'''' under programmed control, as a final path for outputting the microwave transferred from the signal distributor 603 and of which the phase is not shifted.

The high power amplifiers 606', 606", 606''', and 606'''' may correspond to the microwave amplifier 305 and the microwave outputter 306 of FIG. 3. The high power amplifiers 606', 606", 606''', and 606'''' may be connected to a patch A 609, a patch B 610, a patch C 611, and a patch D 612, respectively. Each of the high power amplifiers 606', 606", 606''', and 606'''' may amplify the microwave that is switched and transferred from the signal distributor 606', 606". The high power amplifiers 606', 606", 606''', and 606'''' may output the amplified microwaves to the patch A 609, the patch B 610, the patch C 611, and the patch D 612, respectively. The microwave may be transferred from each of the patch A 609, the patch B 610, the patch C 611, and the patch D 612 toward direction 614 corresponding to the deep portion of the body tissue of the user.

Figure 7:
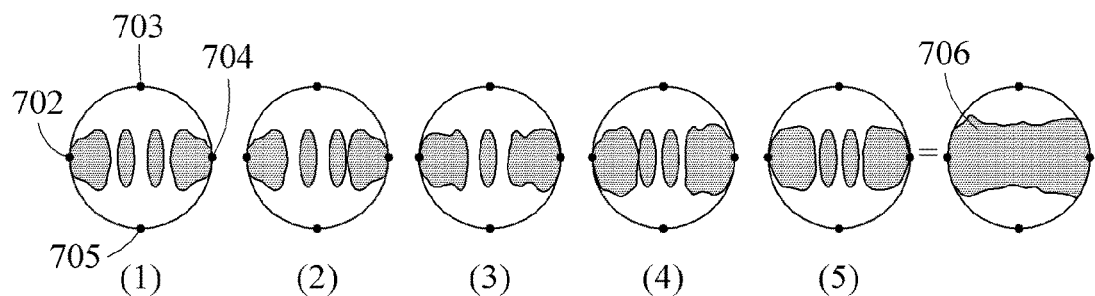
FIG. 7 illustrates an example of a heat distribution area and a heat maintenance area of heat generated in a deep portion of a body tissue of a user using a device for microwave hyperthermia according to an example embodiment.

FIG. 7 illustrates an example of a heat distribution area and a heat maintenance area of heat generated in a deep portion of a body tissue of a user using a device for microwave hyperthermia according to an example embodiment.

According to example embodiments, as a phase of a microwave shifts and a signal path of the phase-shifted microwave switches, a point (also, referred to as a deep heat generation point) at which heat is generated in the deep portion of the body tissue of the user and a point (also, referred to as a radio heat generation point) at which heat is generated in the body tissue due to the heat generated by mismatching on the skin surface may vary and such radio heat generation points may overlap. That is, radio heat generation points according to the respective timings of the treatment mode may vary and may overlap over time. Accordingly, an area 706 in which a warm heat effect occurs within the deep portion by microwaves may be formed.

Herein, a case in which a phase of a microwave is shifted based on an interval of 90 degrees, such as zero degrees, 90 degrees, 180 degrees, 270 degrees, and 360 degrees, is described as a phase-shift example for generating the heat in the deep portion.

FIG. 7 shows results of setting a phase-shift interval as 90 degrees, such as zero degrees, 90 degrees, 180 degrees, 270 degrees, and 360 degrees, and sequentially shifting a phase of a microwave in order of <(1), (2), (3), (4), (5)> of the treatment mode.

Referring to FIG. 7, the treatment mode may be in a state programmed to emit a microwave toward a patch A 703 and a patch C 705 and to not emit a microwave toward a patch B 704 and a patch D 702.

The device for microwave hyperthermia may combine a phase shift of the microwave and a state change of signal switching, and may emit the microwave toward the deep portion of the body tissue sequentially in temporal order from timing t1 to timing t5. The emitted microwaves may generate the heat at specific points of the deep portion of the body tissue and radio heat generation points may move. The radio heat generation points may overlap and a warm heat effect may occur over the entire area within the deep portion. That is, an area 706 in which the radio heat is distributed and maintained according to a treatment mode A 701 may be formed.

Figure 8:
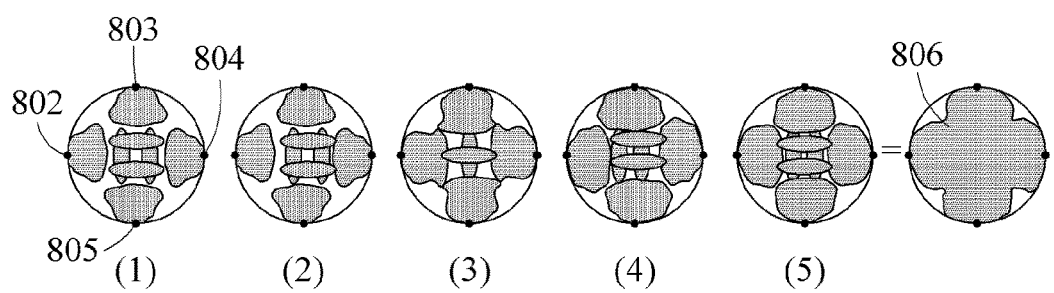
FIG. 8 illustrates another example of a heat distribution area and a heat maintenance area of heat generated in a deep portion of a body tissue of a user using a device for microwave hyperthermia according to an example embodiment.

FIG. 8 illustrates another example of a heat distribution area and a heat maintenance area of heat generated in a deep portion of a body tissue of a user using a device for microwave hyperthermia according to an example embodiment.

FIG. 8 shows results of setting a phase-shift interval as 90 degrees, such as zero degrees, 90 degrees, 180 degrees, 270 degrees, and 360 degrees, and sequentially shifting a phase of a microwave in order of <(1), (2), (3), (4), (5)> of a treatment mode.

Referring to FIG. 8, the treatment mode may be in a state programmed to initially emit a microwave toward a patch A 802 and a patch B 803 and then stop emitting of the microwave toward the patch A 802 and the patch B 803 and emit the microwave toward a patch C 804 and a patch D 805.

The device for microwave hyperthermia may combine a phase shift of the microwave and a state change of signal switching, and may emit the microwave toward the deep portion of the body tissue sequentially in temporal order from timing t1 to timing t10. The emitted microwaves may generate the heat at specific points of the deep portion of the body tissue and radio heat generation points may move. The radio heat generation points may overlap and a warm heat effect may occur within the deep portion. That is, an area 806 in which the radio heat is distributed and maintained according to a treatment mode B 801 may be formed.

The components described in the example embodiments may be achieved by hardware components including at least one DSP (Digital Signal Processor), a processor, a controller, an ASIC (Application Specific Integrated Circuit), a programmable logic element such as an FPGA (Field Programmable Gate Array), other electronic devices, and combinations thereof. At least some of the functions or the processes described in the example embodiments may be achieved by software, and the software may be recorded on a recording medium. The components, the functions, and the processes described in the example embodiments may be achieved by a combination of hardware and software.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The components described in the example embodiments may be achieved by hardware components including at least one DSP (Digital Signal Processor), a processor, a controller, an ASIC (Application Specific Integrated Circuit), a programmable logic element such as an FPGA (Field Programmable Gate Array), other electronic devices, and combinations thereof. At least some of the functions or the processes described in the example embodiments may be achieved by software, and the software may be recorded on a recording medium. The components, the functions, and the processes described in the example embodiments may be achieved by a combination of hardware and software.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A device for microwave hyperthermia, the device comprising:
   a power device configured to supply power;
   a user input device configured to receive an input on a treatment mode of the device for microwave hyperthermia for treating an affected area present in a body tissue of a user; and a microwave control device configured to control a microwave for generating a heat in a deep portion of the body tissue through n patches attached on the skin of the user, wherein the microwave control device is configured to control the microwave to shift a phase of the microwave emitted in each of directions in which the n patches are attached on the skin of the user shifts based on the treatment mode, and the phase of the microwave changes a generation location and a distribution range of heat from the skin of the user to the deep portion of the body tissue.

2. The device of claim 1, wherein the microwave control device comprises:
a microwave generator configured to generate the microwave;
a phase shifter configured to shift the phase of the microwave based on the treatment mode;
a switcher configured to switch at least one of the n patches to emit the phase-shifted microwave; and
a microwave outputter configured to output the phase-shifted microwave through a cable that is connected to each of the switched at least one patch.

3. The device of claim 2, wherein the phase shifter is configured to shift the phase of the microwave emitted in each of the directions to have a desired phase difference at each timing at which the microwave is output within an operation time of the treatment mode.

4. The device of claim 3, wherein the phase shifter is configured to shift the phase of the microwave based on the phase of the microwave that is to be output through each of the n patches based on each corresponding timing.

5. The device of claim 2, wherein the switcher is configured to switch a direction in which the microwave is emitted so that the phase-shifted microwave is output through at least one of the n patches based on each corresponding timing.

6. The device of claim 2, wherein the microwave outputter is configured to amplify the phase-shifted microwave and to output the amplified microwave through the cable that is connected to each of the switched at least one patch.

7. The device of claim 2, wherein each of the n patches is configured to receive the microwave of which the phase is shifted based on the treatment mode, and to emit the received microwave from the skin of the user toward the inside of the body tissue.

8. The device of claim 7, wherein the microwave is emitted through at least one of the n patches and has the same phase at a plurality of points occurring in the deep portion of the body tissue.

9. A patch configured to connect to a device for microwave hyperthermia, the patch comprising:
a surface cover configured to control a microwave transferred through a cable that is connected to the device for microwave hyperthermia;
a patch antenna comprising a dielectric configured to transfer the microwave to a deep portion of a body tissue of a user; and
a contactor configured to contact the surface cover and to transfer the microwave reflected from the surface cover to the patch antenna,
wherein the patch is configured to emit a microwave having a desired phase difference toward the deep portion of the body tissue based on each timing at which the microwave is output based on a treatment mode of the device for microwave hyperthermia.

10. The patch of claim 9, wherein the surface cover is configured to block leakage of the microwave to be emitted toward the deep portion of the body tissue of the user or to reflect the microwave toward the deep portion of the body tissue.

11. The patch of claim 9, wherein the dielectric performs radio frequency (RF) matching between the patch antenna and the skin of the user and comprises a medium for providing thermoelectric cooling or water cooling by heat exchange on the skin of the user.

12. The patch of claim 9, wherein an adhesive material is applied on one surface of the patch antenna to be attached on the skin of the user.

13. A microwave control device included in a device for microwave hyperthermia, the microwave control device comprising:
a microwave generator configured to generate a microwave based on a treatment mode of the device for microwave hyperthermia for treating an affected area present in a body tissue of a user;
a phase shifter configured to shift a phase of the microwave emitted in each of directions in which n patches are attached on the skin of the user based on the treatment mode;
a switcher configured to switch at least one of the n patches to emit the phase-shifted microwave;
a microwave amplifier configured to amplify the phase-shifted microwave; and
a microwave outputter configured to output the amplified microwave through a cable that is connected to each of the switched at least one patch,
wherein the phase shifter is configured to shift the phase of the microwave emitted in each of the directions to have a desired phase difference at each timing at which the microwave is output within an operation time of the treatment mode.

14. The microwave control device of claim 13, wherein the phase shifter is configured to shift the phase of the microwave based on the phase of the microwave that is to be output through each of the n patches based on each corresponding timing.

15. The microwave control device of claim 13, wherein the phase of the microwave changes a generation location and a distribution range of heat from the skin of the user to the deep portion of the body tissue.

16. The microwave control device of claim 13, wherein the switcher is configured to switch a direction in which the microwave is emitted so that the phase-shifted microwave is output through at least one of the n patches based on each corresponding timing.

17. The microwave control device of claim 13, wherein each of the n patches is configured to receive the microwave of which the phase is shifted based on the treatment mode, and to emit the received microwave from the skin of the user toward the inside of the body tissue.

18. The microwave control device of claim 17, wherein the microwave is emitted through at least one of the n patches and has the same phase at a plurality of points occurring in the deep portion of the body tissue.

* * * * *